United States Patent [19]

Arneklev et al.

[11] 4,021,229
[45] May 3, 1977

[54] SULFONAMIDE HERBICIDE ANTIDOTE COMPOSITIONS AND METHOD OF USE

[75] Inventors: Duane R. Arneklev, Antelope, Mont.; Don R. Baker, Orinda, Calif.

[73] Assignee: Stauffer Chemical Company, Westport, Conn.

[22] Filed: Sept. 5, 1972

[21] Appl. No.: 285,971

[52] U.S. Cl. .................................. 71/100; 71/88; 71/103
[51] Int. Cl.² ................................... A01N 9/12
[58] Field of Search .......... 71/100, 103; 260/556 A

[56] References Cited

UNITED STATES PATENTS

| | | | |
|---|---|---|---|
| 2,927,126 | 3/1960 | Pursglove | 71/103 |
| 3,131,509 | 5/1964 | Hoffmann | 71/77 |
| 3,300,529 | 1/1967 | Berkelhammer et al. | 260/556 A |
| 3,549,703 | 12/1970 | Tishler et al. | 260/556 A |
| 3,564,768 | 2/1971 | Hoffman | 47/57.6 |
| 3,719,466 | 3/1973 | Ahle | 71/88 |

OTHER PUBLICATIONS

Nys et al. I, "Polymethine Dyes" (1958), ca 56, pp. 13705–13707 (1962).
Nys et al. II, "Sensitization of Photographic Silver Halide Emulsions" (1960), ca 57, pp. 328–331 (1962).

*Primary Examiner*—Glennon H. Hollrah
*Attorney, Agent, or Firm*—Harry A. Pacini

[57] ABSTRACT

Herbicidal compositions consisting of an active herbicidal compound and an antidote therefor and the methods of use of the herbicide compositions are described herein. The antidote compound corresponds to the formula

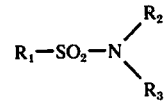

wherein $R_1$ can be selected from the group consisting of alkyl, haloalkyl, halogen, isocyanate, alkenylamino, halophenylamino, phenyl, substituted phenyl wherein said substituents can be selected from alkyl, alkoxy, halogen, nitro, amino and haloalkylaminosulfonyl; $R_2$ and $R_3$ can be the same or different and can be selected from hydrogen, alkyl, haloalkyl, alkoxy, alkenyl, alkynyl, alkynoxy, haloalkoxycarbonyl, alkynoxycarbonyl, carbamoyl, haloalkylthio, diacetonitrilocarbamyl, phenyl, substituted phenyl wherein said substituents can be selected from alkoxy, halogen, hydroxy, nitro and carbamoyl, and $R_2$ and $R_3$ taken together form the ring structure alkyloxazolidyl.

13 Claims, No Drawings

SULFONAMIDE HERBICIDE ANTIDOTE COMPOSITIONS AND METHOD OF USE

BACKGROUND OF THE INVENTION

Among the many herbicidal compounds commercially available, the thiocarbamates, alone or admixed with other herbicides such as the triazines, have reached a relatively high degree of commercial success. These herbicides are immediately toxic to a large number of weed pests at different concentrations varying with the resistance of the weed pests. Some examples of these compounds are described and claimed in the U.S. Pat. No. 2,913,327, 3,037,853, 3,175,897, 3,185,720, 3,198,786, and 3,582,314.

It has been found in practice that the use of these thiocarbamates as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. No. 3,131,509 and 3,564,768. These antagonistic agents have not been notably successful.

The aforementioned patent specifically exemplifies the treatment of seeds employing compounds of a different chemical class not suggestive of the present invention.

DESCRIPTION OF THE INVENTION

It has been discovered that plants can be protected against injury by the thiocarbamates alone or mixed with other compounds and/or the tolerance of the plants can be substantially increased to the active compounds of the above-noted U.S. Pats. by adding to the soil an antidote compound corresponding to the following formula

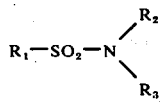

wherein $R_1$ can be selected from the group consisting of alkyl, haloalkyl, halogen, isocyanate, alkenylamino, halophenylamino, phenyl, substituted phenyl wherein said substituents can be selected from alkyl, alkoxy, halogen, nitro, amino and haloalkylaminosulfonyl; $R_2$ and $R_3$ can be the same or different and can be selected from hydrogen, alkyl, haloalkyl, alkoxy, alkenyl, alkynyl, alkynoxy, haloalkoxycarbonyl, alkynoxycarbonyl, carbamoyl, haloalkylthio, diacetonitrilocarbamyl, phenyl, substituted phenyl wherein said substituents can be selected from alkoxy, halogen, hydroxy, nitro and carbamoyl, and $R_2$ and $R_3$ taken together form the ring structure alkyloxazolidyl.

In the description of the sulfonamide compounds useful in the herbicidal antidote method of this invention, the following embodiments are intended for the various groups: Alkyl preferably includes those members containing from 1 to 6 carbon atoms, inclusive, in both branched and straight chain configuration; alkenyl preferably includes those members which contain at least one olefinic double bond and from 3 to 6 carbon atoms, inclusive, in both branched and straight chain configurations; alkynyl perferably includes those members which contain at least one acetylinic triple bond and from 3 to 5 carbon atoms, inclusive, in both branched and straight chain configurations. The term halo and halogen preferably includes chloro and chlorine, bromo and bromine, and fluoro and fluorine. When used in a substituent for substituted phenyl, the terms alkyl, alkoxy and haloalkylaminosulfonyl preferably each independently include those members having from 1 to 4 carbon atom, inclusive. The alkyl substituents in alkyloxazolidyl preferably include those members having from 1 to 4 carbon atoms, inclusive, said alkyl members may be present as mono, di, tri or tetra-substituents.

The compounds represented by the above formula can be synthesized by mixing together an appropriate acid chloride with an appropriate alcohol or amine. A solvent can be used if desired. The reaction is exothermic so cooling may be required. After the reaction is complete, the end product is readily recovered by normal work-up procedures, such as crystallization, sublimation or distillation.

In order to illustrate the preparation of the compounds of the present invention, reference is made to the following examples.

EXAMPLE 1

Preparation of Benzenesulfono-2-fluoroanilide 17.6 g. of benzenesulfonyl chloride was mixed with 11.1 g. of ortho-fluoro aniline and 15 ml. of triethylamine and stirred together. An exothermic reaction took place. After this reaction subsided, the mixture was washed with water, dilute hydrochloric acid and additional water. The product was collected on a filter and air dried to yield 19.0 g. of product, m.p. 62°–65° C.

EXAMPLE 2

Preparation of N-(2,4,5-trichlorophenyl)-methane sulfonamide

A mixture of 2,4,5-trichloroaniline (39.3 g.), methane sulfonyl chloride (22.9 g.) and 100 ml. of xylene were heated together under reflux conditions for 18 hours. The mixture was then allowed to cool, which formed a brown precipitate. The product was worked up in the same manner as set forth in Example 1 to yield 24.0 g. of product, m.p. 144°–145° C.

EXAMPLE 3

Preparation of N-(β-chloroethyl)-benzene sulfonamide 40.2 g. of N-(β-hydroxyethyl)-benzene sulfonamide was slurried in 100 ml. of carbon tetrachloride containing 5 drops of piperidine. Then, 47.6 g. of sulfonyl chloride was added over 10 minutes, keeping the temperature at 20°–25° C. during the addition. The reaction was completed by heating on a steam bath for one hour. The mixture was concentrated on the steam bath, dissolved in benzene and washed twice with dilute aqueous solution of sodium chloride, dried over magnesium sulfate, filtered and the benzene evaporated on the steam bath with air. The product was crystallized from benzene cyclohexane to yield 28.0 g. of product, m.p. 58°–62° C.

EXAMPLE 5

Preparation of N-propargyl benzenesulfonamide

To 8.6 g. piloty acid dissolved in 50 ml. methanol, propargyl bromide (6.6 g.) was added. 10.8 g. sodium methoxide (25%) was added slowly dropwise. An exothermic reaction resulted, the temperature was maintained at 30° C. The reaction mixture was stirred for approximately 1 hour at room temperature. The solvent was removed in vacuo. There was obtained a yellow solid. This material was treated with ether and the solid filtered off and dried. There was obtained 3.1 g. of the title compound, a low melting solid.

EXAMPLE 6

Preparation of N-methoxy-2,4,5-trichlorobenzenesulfonamide 5.0 g. of methoxy amine was dissolved in 100 ml. of $H_2O$. Then, 14.0 g. of 2,4,5-trichlorobenzene sulfonyl chloride dissolved in 25 ml. of tetrahydrofuran was added under high speed mechanical stirring. Then, 8.8 g. of sodium hydroxide in a 50% solution + 10 ml. of water was dropped in at room temperature. An exothermic reaction took place and the temperature went up to 37.5° C. When the reaction subsided, it was stirred at room temperature for two hours and the solid was then filtered off and stirred into 150 ml. of ether for one hour. The solid was removed by filtration to yield 11.3 g. of product. The product was redissolved in ether. The ether was evaporated to yield 7.4 g. of product, m.p. 163°–166° C.

EXAMPLE 7

Preparation of 0-(3-bromopropyl)-N-chlorosulfonylcarbamate

A solution was formed containing 4.5 ml. of 3-bromo-1-propanol in 100 ml. of ether. Then, 7.0 g. of chlorosulfonyl isocyanate was added over a period of one minute with stirring. The temperature rose to boiling. After standing overnight, a small amount of solid was filtered off and the solvent was then evaporated off to yield 12.3 g. of product, $n_D^{30} = 1.4903$.

EXAMPLE 8

Preparation of N,N-diallyl-isobutylsulfonamide

A solution was formed containing 19.4 g. of diallylamine in 100 ml. of benzene. Then, 15.7 g. of isobutylsulfonyl chloride was added at such a rate that the temperature did not exceed 45° C. The mixture was stirred and refluxed for ten minutes, cooled, washed with 100 ml. of dilute hydrochloric acid and then with $H_2O$. It was then dried over magnesium sulfate, filtered and evaporated to give 20.1 g. (02% of theory) of the product, a liquid, $n_D^{30} = 1.4697$.

EXAMPLE 9

Preparation of 2-ethyl-3-methylsulfonyl-5-methyl oxazolidine

A solution was formed containing 25 ml. of benzene and 6 g. of 2-ethyl-5-methyl oxazolidine suspended in 24 ml. of benzene. Then, 5.5 g. of triethylamine was added. The solution was cooled in an ice bath, wherein 5.8 g. of methane sulfonyl chloride was added dropwise with stirring to yield 6.4 g. of product, $n_D^{30} = 1.4778$.

EXAMPLE 10

Preparation of N-(1,1,2-trichloro-2-propylthio)-N-phenyl ethanesulfonamide

To a stirred, cooled solution of 18.5 g. of N-phenyl ethane sulfonamide in 10.1 g. of triethylamine and 200 ml. of chloroform was added at a temperature below 10° C. a solution of 1,1,2-trichloropropane-2-sulfonyl chloride (21.4 g.) in 50 ml. of chloroform. During the addition, an exothermic reaction took place. When the addition was complete, the mixture was allowed to cool to room temperature. The product was washed twice with water, dried over sodium sulfate and filtered and stripped. A viscous red oil was formed which on evaporation with benzene yielded a solid product of 29.6g. (92% of theory), m.p. 85°–86° C.

EXAMPLE 11

Preparation of N,N-dipropyl sulfonylchloride 270 g. of sulfonyl chloride was mixed with 500 ml. of benzene in a 200 ml. 3-necked flask. The mixture was stirred and cooled with an ice bath to below 10° C. Then, 404.4 g. of n-dipropylamine was added dropwise. An exothermic reaction took place. The temperature was kept under 20° C. After three hours the reaction was complete. A clear yellow gel-like product was formed. After standing overnight, the product was heated to reflux, dropped into 300 ml. of cold water. This mixture was extracted two times with 150 ml. of benzene. The benzene was washed three times with 250 ml. of water. The organic solution was dried with magnesium sulfate and stripped to yield 272.2 g. of product, $n_D^{30} = 1.4547$.

EXAMPLE 12

Preparation of 2-bromoethyl methanesulfonamide

Triethylamine (56 ml., 0.40 mole) was added over a period of 1 hour at 10° to 20° C. to a mixture of methanesulfonyl chloride (15.2 ml., 0.20 mole), 2-bromoethylamine hydrobromide (41 g., 0.20 mole) in 200 ml. of chloroform. The resulting mixture was stirred for a period of about 1 hour, then concentrated in vacuo. The semi-solid was washed with 500 ml. of benzene. The benzene was evaporated in vacuo to an oil. The soil was diluted with 200 ml. of acetone and filtered through sodium bicarbonate. The solvent was evaporated in vacuo to give an oil (35 g.). The first solid obtained was washed with 200 ml. of acetone and evaporated in vacuo. An additional 4.8 g. of an oil was obtained. The title product was obtained, $n_D^{30} = 1.5012$.

EXAMPLE 13

Preparation of N-(3-bromopropyl) methanesulfonamide

To a cooled solution of 2-bromopropylamine hydrobromide (43.8 g., 0.20 mole) in pyridine (100 ml.) was added over a period of 40 minutes methanesulfonyl chloride (15.2 ml., 0.20 mole). The reaction mixture was stirred for 15 minutes and then diluted with ether. The remaining solid was filtered off, washed with about 200 ml. of acetone. The filtrate and washes were concentrated in vacuo. The residue was extracted with three 100 ml. portions of acetone. Upon evaporation of the acetone, 30.4 g. of a thick oil representing the title compound. The product was confirmed by infrared analysis and nuclear magnetic resonance.

EXAMPLE 14

Preparation of 2-bromoethyl chloromethanesulfonamide

Pyridine (17.8 ml.) was added over a period of 30 minutes to a cooled solution (15 – 20° C.) of 2-bromoethylamine hydrobromide (20.5 g., 0.10 mole) and chloromethanesulfonyl chloride (14.9 g., 0.10 mole) in chloroform. The mixture was stirred for 1 hour and then washed with water (100 ml.) and dilute hydrochloric acid (50 ml.). The solution was dried over magnesium sulfate. The solvent was evaporated in vacuo. There was obtained 10 g. of a dark oil, the title compound. Structure was confirmed by infrared analysis.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I $$R_1-SO_2-N{<}^{R_2}_{R_3}$$

| COMPOUND NUMBER | $R_1$ | $R_2$ | $R_3$ | m.p. ° C. or $n_D^{30}$ |
|---|---|---|---|---|
| 1 | phenyl | H | 4-F-phenyl | 62–65 |
| 2 | —CH$_3$ | H | 2,4,5-trichlorophenyl | 143.5–145 |
| 3 | 4-NO$_2$-phenyl | H | 2-Cl-phenyl | 125–126 |
| 4 | 3-NO$_2$-phenyl | H | 2-Cl-phenyl | 150.5–152 |
| 5 | phenyl | H | phenyl | 107.3–110.1 |
| 6 | phenyl | H | 2-OCH$_3$-phenyl | 76–78 |
| 7 | phenyl | H | 2-NO$_2$-phenyl | 111–115 |
| 8 | phenyl | H | 2-(C(O)NH$_2$)-phenyl | 133–140 |
| 9 | 4-CH$_3$-phenyl | H | 4-F-phenyl | 1.5614 |
| 10 | 4-Cl-phenyl | H | 3-F-phenyl | 186–191 |
| 11 | 4-OCH$_3$-phenyl | H | 3-F-phenyl | 96–100 |
| 12 | 4-Cl-phenyl | H | 2-OH-phenyl | 83–84 |

TABLE I-continued $$R_1-SO_2-N\begin{smallmatrix}R_2\\R_3\end{smallmatrix}$$

| Compound Number | R₁ | R₂ | R₃ | m.p. °C. or $n_D^{30}$ |
|---|---|---|---|---|
| 13 | phenyl | H | 2-methylphenyl | 123.5–128 |
| 14 | —CH₃ | H | 2,3-dichlorophenyl | 163–165 |
| 15 | —CH₃ | H | 2,6-dichlorophenyl | 90–93 |
| 16 | 4-fluorophenyl | H | phenyl | 180–182 |
| 17 | 2-aminophenyl | H | 4-chlorophenyl | 126–130 |
| 18 | phenyl | H | H | 156 |
| 19 | —CH₃ | H | H | 87–89 |
| 20 | phenyl | H | —C₂H₄Cl | 58–62 |
| 21 | 4-methylphenyl | H | —C(O)—O—CH₂C≡CCH₃ | 128–130 |
| 22 | phenyl | H | —O—CH₂C≡CH | semi-solid |
| 23 | 2,4,5-trichlorophenyl | H | —OCH₃ | 163–166 |
| 24 | 2,4,5-trichlorophenyl | —CH₃ | —CH(CH₃)—C≡CH | 84.5–89 |
| 25 | —CH₃ | H | —C₂H₄Cl | $n_D^{25}$ 1.4820 |
| 26 | —CH₃ | H | —C₂H₄Br | 1.5012 |
| 27 | Cl | H | —O—C(O)—C₂H₄Br | 1.4778 |
| 28 | Cl | H | —C(O)—O—C₂H₄Br | 1.4903 |
| 29 | —CH₃ | H | —C₃H₆Br | semi-solid |
| 30 | —C₂H₅ | phenyl | —S—C(Cl)(CH₃)CHCl₂ | 85–86 |
| 31 | —CH₃ | 2-methoxyphenyl | —S—CH(Cl)CHCl₂ | 104–109 |
| 32 | i—i-C₄H₉ | —CH₂—CH=CH₂ | —CH₂—CH=CH₂ | 1.4697 |
| 33 | 4-nitrophenyl | —CH₂—CH=CH₂ | —CH₂—CH=CH₂ | 62–66 |
| 34 | —NCO | —CH₂—CH=CH₂ | —CH₂—CH=CH₂ | 1.5064 |
| 35 | Cl | H | —C(O)—N(CH₂C≡N)₂ | 39–47 |
| 36 | phenyl | —C₂H₄Cl | —C₂H₄Cl | 45–46 |
| 37 | phenyl | H | —C(O)—NH₂ | 178–179 |

TABLE I-continued $$R_1-SO_2-N\begin{matrix}R_2\\R_3\end{matrix}$$

| COMPOUND NUMBER | $R_1$ | $R_2$ | $R_3$ | m.p. °C. or $n_D^{30}$ |
|---|---|---|---|---|
| 38 | Cl | $-n-C_3H_7$ | $-n-C_3H_7$ | 1.4547 |
| 39 | $-NH-\langle\bigcirc\rangle-F$ | $-CH_3$ | $-CH_3$ | 82–83 |
| 40 | $-C_3H_6Cl$ | $-CH_2-CH=CH_2$ | $-CH_2-CH=CH_2$ | reddish brown liquid |
| 41 | $-C_3H_6Cl$ | H | $-t-C_4H_9$ | 67–69 |
| 42 | $-N(CH_2CH=CH_2)_2$ | $-CH_2-CH=CH_2$ | $-CH_2-CH=CH_2$ | 1.4840 |
| 43 | $-CH_3$ |  | $\overset{CH_3}{\underset{C_2H_5}{\langle\,\,\,O}}$ | 1.4778 |
| 44 | $-C_2H_5$ | H | $-C_2H_4Br$ | 1.5166 |
| 45 | $-n-C_3H_7$ | H | $-C_2H_4Br$ | 1.4916 |
| 46 | $-CH_2Cl$ | H | $-C_2H_4Br$ | thick oil |
| 47 | $-i-C_4H_9$ | H | $-C_2H_4Br$ | 1.4965 |
| 48 | $\langle\bigcirc\rangle-SO_2-NHC_2H_4Br$ | H | $-C_2H_4Br$ | 81–84 |
| 49 | $\langle\bigcirc\rangle-Cl$ | $-CH_3$ | $-CH(CH_3)C\equiv CH$ | 107–109 |

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant speciies which can be protected by this method is not intended to be limited by the specific crops employed in the examples.

The herbicidal compounds employed in the method of this invention are active herbicides of a general type. That is, the members of the classes are herbicidally effective against a wide range of plant species with no discrimination between desirable and undesirable species. The method of controlling vegetation comprises applying an herbicidally effective amount of the herein-described herbicidal compounds to the area or plant locus where control is desired.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

The herbicidal active compositions of this invention comprising thiocarbamates in combination with antidote compounds described hereinabove were tested in the following manner.

Corn Seed Treatment Test

Small flats were filled with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals 1 pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six DeKalb XL 374 field corn seeds were planted in each row. Rows were approximately 1½ inches apart in the flat. Seeds were treated by placing 50 mg. of the antidote compound with 10 grams of corn seed in a suitable container and shaking them until the seeds were uniformly covered with the compound. Antidote compounds were also applied as liquid slurries and powders or dusts. In some cases, acetone was used to dissolve powdered or solid compounds so they could be more effectively applied to the seeds.

After the flats were seeded, they were covered with the one pint of soil which had beem removed just prior to planting. Flats were placed on greenhouse benches where temperatures ranged from 70°–90° F. Flats were watered by sprinkling as needed to assure good plant growth. Per cent control ratings were taken two to three weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control. The results of these tests are tabulated in Table II.

TABLE II

Per Cent Injury to Corn from EPTC*
Seed Treatment Test

| COMPOUND NUMBER | EPTC lb/A | Per Cent Injury, 2 weeks Treated Seed (0.5% w/w) | Untreated Seed Adjacent Row |
|---|---|---|---|
| 1 | 4 | 5 | 98 |
| 2 | 4 | 5 | 98 |
| 3 | 4 | 40 | 98 |
| 4 | 4 | 60 | 98 |
| 5 | 4 | 20 | 98 |
| 6 | 4 | 40 | 98 |
| 7 | 4 | 50 | 98 |
| 8 | 4 | 15 | 98 |
| 9 | 4 | 30 | 98 |
| 10 | 4 | 20 | 98 |
| 11 | 4 | 20 | 98 |
| 12 | 4 | 30 | 98 |
| 13 | 4 | 15 | 98 |
| 14 | 4 | 25 | 98 |
| 15 | 4 | 10 | 98 |
| 16 | 4 | 60 | 98 |
| 17 | 6 | 45 | 90 |
| 18 | 6 | 65 | 98 |
| 19 | 6 | 50 | 98 |
| 20 | 6 | 10 | 98 |
| 21 | 6 | 10 | 98 |
| 22 | 6 | 20 | 98 |
| 23 | 6 | 75 | 98 |
| 24 | 6 | 65 | 98 |
| 25 | 6 | 37 | 98 |
| 26 | 6 | 0 | 98 |
| 27 | 6 | 30 | 98 |
| 28 | 6 | 0 | 98 |
| 29 | 6 | 5 | 98 |
| 34 | 6 | 10 | 98 |
| 35 | 6 | 60 | 98 |
| 44 | 6 | 0 | 98 |
| 45 | 6 | 0 | 98 |
| 46 | 6 | 15 | 98 |
| 47 | 6 | 0 | 98 |
| 48 | 6 | 30 | 98 |
| 49 | 6 | 60** | 80 |

* = S-ethyl dipropylthiocarbamate
** = Seed treatment 0.05%

Soil Incorporation Test

Small flats were filled with Felton loamy sand soil. The herbicide and herbicide antidote were applied separately or in combination to the soil as it is mixed in a 5-gallon cement mixer. The following stock solutions were made up of each compound when the herbicide and antidote were applied separately. Stock solutions of the herbicide were diluted with 100 ml. of water. For the antidote, 700 mg. of technical material was diluted with 100 ml. of acetone. 1 ml. of these stock solutions is equivalent to 7 mg. active ingredient or 1 pound per acre when this treated soil was placed into 8 × 12 × 3 inch flats. After the soil was treated with the herbicide and the antidote at the desired rates, the soil was transferred from the cement mixer back into 8 × 12 × 3 inch flats where it was now ready for planting corn seed. A pint sample of soil was then removed from each flat and retained for covering the seeds after planting. The soil was leveled and rows one-half inch deep were made in each flat. Enough seeds were planted to obtain good stands in each treatment. Seeds were then covered up with the one pint of soil which had been removed just prior to planting.

The flats were then placed on greenhouse benches where temperatures were between 70°–90° F. The flats were watered by sprinkling as needed to assure good plant growth until rated. The crop tolerance were rated after 3 to 6 weeks. The results of these tests are set forth in Table III.

TABLE III

Per Cent Injury to Corn from EPTC*
Soil Incorporation Test

| COMPOUND NUMBER | EPTC lb/A | Antidote 5 lb/A Preplant Incorporated | Untreated Planting Area |
|---|---|---|---|
| 30 | 3 | 0 | 80 |
| 31 | 3 | 70 | 80 |
| 32 | 3 | 60 | 80 |
| 33 | 3 | 40 | 80 |
| 34 | 3 | 50 | 80 |
| 36 | 3 | 40 | 60 |
| 37 | 3 | 10 | 80 |
| 38 | 3 | 60 | 80 |
| 39 | 3 | 20 | 80 |
| 40 | 5 | 30 | 70 |
| 41 | 5 | 0 | 70 |
| 41** | 5 | 40*** | 50*** |
| 42 | 5 | 0 | 70 |
| 43 | 5 | 30 | 70 |

*EPTC = S-ethyl dipropylthiocarbamate
** = Antidote candidate at 1/20 lb/A
*** = Corn variety employed PAG 344T field corn The antidote compounds of the present invention can be used in any convenient form. Thus, the antidote compounds can be made into emulsifiable liquids, emulsifiable concentrates, liquid, wettable powder, powders, granular or any other convenient form. In its preferred form, a non-phytotoxic quantity of an antidote compound is admixed with the selected thiocarbamates and incorporated into the soil prior to or after planting the seed. It is to be understood, however, that the thiocarbamate herbicide can be incorporated into the soil and thereafter the antidote compound can be incorporated into the soil. Moreover, the seed can be treated with a non-phytotoxic quantity of the antidote compound and planted into the soil which has been treated with herbicides or untreated with the herbicide and subsequently treated with the herbicide. The addition of the antidote compound does not affect the herbicidal activity of the carbamate compounds.

The amount of antidote composition present can range between about 0.01 to about 15 parts by weight of antidote compound described herein per each part by weight of thiocarbamate herbicide. The exact amount of antidote compound will usually be determined on economic ratios for the most effective amount usuable. It is understood that a non-phytotoxic quantity of antidote compound will be employed in the herbicidal compositions and method of this invention.

What is claimed:

1. A herbicide composition comprising a mixture of a thiocarbamate herbicide and an antidotally effective amount of an antidote compound corresponding to the formula

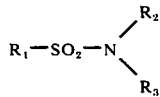

wherein $R_1$ is selected from the group consisting of alkyl containing from 1 to 6 carbon atoms, inclusive, haloalkyl having from 1 to 6 carbon atoms, inclusive; $R_2$ and $R_3$ can be the same or different and are selected from the group consisting of hydrogen, haloalkyl containing from 1 to 6 carbon atoms, alkenyl containing from 3 to 6 carbon atoms, inclusive wherein said antidote compound is present in an amount ranging between about D01 to about 15 parts by weight of the herbicide compound.

2. The composition according to claim 1 in which $R_1$ is alkyl, $R_2$ is hydrogen and $R_3$ is hydrogen.

3. The composition according to claim 2 in which $R_1$ is methyl.

4. The composition according to claim 1 in which $R_1$ is alkyl, $R_2$ is hydrogen and $R_3$ is haloalkyl.

5. The composition according to claim 4 in which $R_1$ is ethyl and $R_3$ is 2-bromoethyl.

6. The composition according to claim 4 in which $R_1$ is n-propyl and $R_3$ is 2-bromoethyl.

7. The composition according to claim 4 in which $R_1$ is isobutyl and $R_3$ is 2-bromoethyl.

8. The composition according to claim 4 in which $R_1$ is methyl and $R_3$ is 2-chloroethyl.

9. The composition according to claim 4 in which $R_1$ is methyl and $R_3$ is 2-bromoethyl.

10. The composition according to claim 4 in which $R_1$ is methyl and $R_3$ is 3-bromopropyl.

11. The composition according to claim 1 in which $R_1$ is isobutyl, $R_2$ is allyl and $R_3$ is allyl.

12. The composition according to claim 1 in which $R_1$ is 3-chloropropyl, $R_2$ is allyl and $R_3$ is allyl.

13. The composition according to claim 1 in which $R_1$ is 3-chloropropyl, $R_2$ is hydrogen and $R_3$ is t-butyl.

* * * * *

UNITED STATES PATENT AND TRADEMARK OFFICE
CERTIFICATE OF CORRECTION

PATENT NO. : 4,021,229
DATED : May 3, 1977
INVENTOR(S) : Duane R. Arneklev, et al.

It is certified that error appears in the above-identified patent and that said Letters Patent are hereby corrected as shown below:

Column 2, line 4, the word reading "5 carbon atoms" should read ---6 carbon atoms---.

Table I, compound number 32 in $R_1$ column reading "i  i-$C_4H_9$" should read ---i-$C_4H_9$---.

Table I, compound number 48 in $R_1$ column reading

" 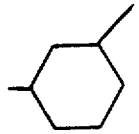 $SO_2$—$NHC_2H_4Br$" should read --- 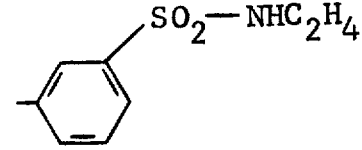 $SO_2$—$NHC_2H_4Br$---

Table I, compound number 40 in $R_2$ column reading "—$CH_2$—CH—$CH_2$" should read ----$CH_2$—CH=$CH_2$---.

Table I, compound number 27 in $R_3$ column reading "—O—$C_2H_4Br$" should read ---$\overset{\overset{O}{\|}}{C}$—O—$C_2H_4Br$---.

Table I, compound number 40 in $R_3$ column reading "—$CH_2$—CH—$CH_2$" should read ----$CH_2$—CH=$CH_2$---.

Column 9, line 44, the word reading "speciies" should read ---species---.

Column 12, line 9, the word reading "were" should read ---was---.

UNITED STATES PATENT AND TRADEMARK OFFICE
CERTIFICATE OF CORRECTION

PATENT NO. : 4,021,229

DATED : May 3, 1977

INVENTOR(S) : Duane R. Arneklev, et al.

It is certified that error appears in the above-identified patent and that said Letters Patent are hereby corrected as shown below:

Table III, compound number 41 in 1b/A column should read ---5---.

Column 13, line 15, "D01" should read ---0.01---

Signed and Sealed this

Fifteenth Day of November 1977

[SEAL]

Attest:

RUTH C. MASON
Attesting Officer

LUTRELLE F. PARKER
Acting Commissioner of Patents and Trademarks